United States Patent [19]

Heiser et al.

[11] Patent Number: 4,861,890

[45] Date of Patent: Aug. 29, 1989

[54] ISOMERIZATION

[75] Inventors: Bernd Heiser, Inzlingen, Fed. Rep. of Germany; Hansjörg Stoller, Reinach, Switzerland

[73] Assignee: Hoffmann-La Roche Inc., Nutley, N.J.

[21] Appl. No.: 83,349

[22] Filed: Aug. 10, 1987

[30] Foreign Application Priority Data

Aug. 21, 1986 [CH] Switzerland ............... 3352/86

[51] Int. Cl.$^4$ .................................... C07D 211/00
[52] U.S. Cl. ................................ 546/184; 546/248; 564/444; 564/463; 548/400; 548/414; 548/415; 548/547; 548/579; 549/220; 556/7; 556/18; 556/21; 556/22
[58] Field of Search ............... 564/444, 463; 546/184, 546/248; 548/400, 547, 579, 414, 415; 556/7, 18, 21, 22; 549/220

[56] References Cited

U.S. PATENT DOCUMENTS

| | | | |
|---|---|---|---|
| 3,857,867 | 12/1974 | Maspero et al. | 556/22 |
| 3,939,188 | 2/1976 | McViker | 556/21 |
| 4,331,818 | 5/1982 | Riley | 556/22 |
| 4,440,936 | 4/1984 | Riley | 564/184 |
| 4,604,474 | 8/1986 | Kumobayashi et al. | 556/7 |
| 4,605,750 | 8/1986 | Kumobayashi et al. | 556/7 |
| 4,695,631 | 9/1987 | Otsuka et al. | 548/400 |

FOREIGN PATENT DOCUMENTS

| | | |
|---|---|---|
| 68506 | 1/1983 | European Pat. Off. . |
| 135392 | 3/1985 | European Pat. Off. . |
| 156607 | 10/1985 | European Pat. Off. . |
| 170470 | 2/1986 | European Pat. Off. . |
| 235450 | 9/1987 | European Pat. Off. . |

OTHER PUBLICATIONS

Tani et al.; Angew, Chemie, 97, 232, (1985).
Tani et al.; J.A.C.S., (1984), 106, 5208–5217.
Tani et al.; Angeu Chem. Inter Ed Engl., 24, (1985), pp. 217–219.

*Primary Examiner*—Paul Lieberman
*Assistant Examiner*—Hoa Van Le
*Attorney, Agent, or Firm*—Jon S. Saxe; George M. Gould; William H. Epstein

[57] ABSTRACT

A process for producing chiral enamines by isomerizing a beta, gamma unsaturated amine with a rhodium-diphosphine complex with the addition of an achiral triarylphosphine and, if desired, hydrolyzing the compound of the enamine I obtained to the corresponding aldehyde.

14 Claims, No Drawings

ISOMERIZATION

SUMMARY OF INVENTION

This invention is directed to a novel process for the manufacture of chiral enamines of the formula

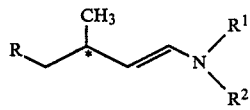   I wherein R is:

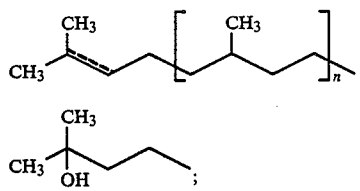

n is the number 0, 1 or 2; the dotted bond can be optionally hydrogenated; and $R^1$ and $R^2$ are lower alkyl or cycloalkyl or when taken together with their attached nitrogen atom form a 5- or 6-membered heterocyclic ring;
and of the corresponding aldehydes, which process comprises isomerizing the E- or Z-form of a compound of the formula

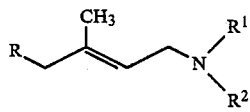   II wherein R, $R^1$ and $R^2$ are as above; with a rhodium-diphosphine complex of the formula $$[Rh(L^1)(L^2)]^+ X^-$$   III wherein $L^1$ is a chiral diphosphine ligand; $L^2$ is a bis-olefin and $X^-$ is a non-complexing anion, with the addition of an achiral triarylphosphine and, if desired, hydrolyzing a thus-obtained compound of formula I.

The invention is also concerned with the complexes obtainable from a rhodium-diphosphine complex of the formula III and an achiral triarylphosphine.

DETAILED DESCRIPTION

The compounds of formula I and the corresponding aldehydes, which are obtained in accordance with the invention, are known intermediates for the manufacture of, inter alia, natural vitamin E, natural vitamin $K_1$ and also odorants.

The compounds I can be easily transformed into an aldehyde of the formula:

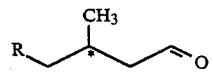

wherein R is as above by hydrolysis with an aqueous acid. The formation of aldehydes from enamines by hydrolysis is well known. This hydrolysis with aqueous acid can take place after the compound of formula I is formed from the compound of formula II or can take place during the work up of the reaction mixture formed after treatment of the compound of formula II with a complex of formula III in accordance with this invention.

The compounds of the formula II which are used as the starting material are known compounds or analogues of known compounds which can be prepared readily in an analogous manner to the known compounds. Such compounds are known, for example, from EP 68 506.

The rhodium-diphosphine complexes of formula III are known complexes and can be prepared according to processes known per se. In accordance with this invention $L^1$ can be any chiral diphosphine ligand. Among the preferred chiral diphosphine ligands are included optically active compounds of the formula which are present in either (R)- or (S)-form

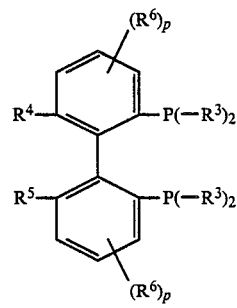   IV wherein $R^3$ is phenyl; $R^4$ and $R^5$, which can be the same or different, are hydrogen, lower alkyl, lower alkoxy, di-lower alkylamino or protected hydroxymethyl; or $R^5$ and $R^6$ taken together form the groups

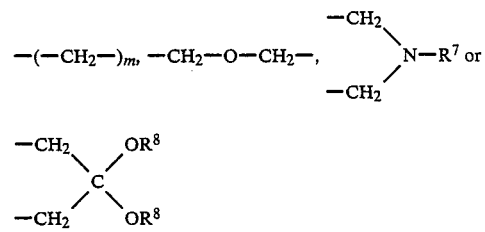

m is a number of from 3 to 5; $R^7$ is lower alkyl, phenyl or benzyl and $R^8$ is lower alkyl or the two $R^8$'s taken together form lower alkylene, $R^6$ is methyl, lower alkoxy, di-lower alkylamino or fluorine; and p is the number 0, 1, 2 or 3, or also optically active compounds of the formula which are present in either the (R)- or (S)-form

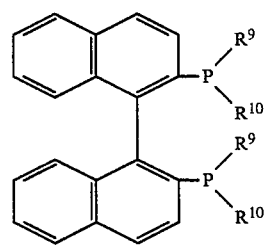   V wherein $R^9$ and $R^{10}$ is phenyl or cyclohexyl; and the naphthalene rings can be unsubstituted or substituted in the ortho-position with methyl, ethyl, halogen, di-lower alkylamino or lower alkoxy.

The term "lower alkyl" signifies especially straight-chain or branched alkyl groups with 1–4 carbon atoms such as methyl, ethyl, propyl, isopropyl, n-butyl, isobutyl and tert.-butyl. The term "cycloalkyl" signifies especially cyclopropyl, cyclopentyl, cyclohexyl and the like. Where the substituents $R^1$ and $R^2$ taken together with the nitrogen atom form a heterocylic ring, this is preferably a pyrrolidine or piperidine ring. However, in such a ring there can also be present a further oxygen atom or an optionally alkylated ($C_1$-$C_4$) or benzylated nitrogen atom, e.g. the morpholine or piperazine ring. The term "non-complexing anion" designates any conventional non-complexing anion. In accordance with the invention any conventional non-complexing anion can be used, especially $BF_4^-$, $PF_6^-$, $ClO_4^-$, $B(phenyl)_4^-$, $PCl_6^-$; etc.

In the formula, the symbol * designates an optically active assymetric carbon atom.

As protecting groups for the hydroxymethyl groups there come into consideration in the scope of the present invention especially the usual hydrolyzable ether-forming groups such as e.g. benzyl, methyl, tert.-butyl, allyl, methoxymethoxy and the like as well as silyl ether-forming groups such as e.g. trimethylsilyl, tert.butyldimethylsilyl and the like. However, any conventional hydrolyzable ether protecting group can be utilized in this reaction.

In the scope of the present invention the aforementioned phenyl and benzyl residues can be not only unsubstituted, but also multiply substituted in the or-thometa- or para-position. The preferred substituents are lower alkyl or lower alkoxy groups, preferably methyl or methoxy groups, or also di-lower alkylamino, preferably dimethylamino, groups, as well as fluorine. The terms "lower alkoxy", "di-lower alkylamino" and "lower alkoxycarbonyl" signify groups in which the alkyl residue can have the previously mentioned significance.

1,5-Cyclooctadiene, 1,5-hexadiene, bicyclo[2.2.1]-hepta-2,5-diene etc are examples of bis-olefins. However, any conventional bis-olefins can be used as the ligand $L^2$.

The compounds of general formulae IV and V are known compounds. Especially preferred compounds of formula IV are those in which $R^3$ is unsubstituted phenyl or methyl- or fluoro-substituted phenyl, $R^4$ and $R^5$ are the same lower alkyl or taken together signify the group —$CH_2$—O—$CH_2$—, p is the number 0 or 1 and $R^6$ signifies methyl, fluorine or di-lower alkylamino. Insofar as p is the number 1, the substituent $R^6$ is preferably situated in the m-position to the phosphorus.

The following can be named as examples of preferred compounds of formula IV:

(R)- or (S)-(6,6'-Dimethyl-2,2'-biphenylylene)bis(diphenylphosphine), (R)- or (S)-(4,4',6,6'-tetramethyl-2,2'-biphenylylene)-bis(diphenylphosphine), (R)- or (S)-(3,3',6,6'-tetramethyl-2,2'-biphenylylene)-bis(diphenylphosphine), (R)- or (S)-(4,4'-bis(dimethylamino)-6,6'-dimethyl-2,2'-biphenylylene)bis(diphenylphosphine), (R)- or (S)-(4,4'-difluoro-6,6'-dimethyl-2,2'-biphenylylene)bis(diphenylphosphine), (R)- or (S)-(6,6'-dimethyl-2,2'-biphenylylene)bis(di-p-tolylphosphine), (R)- or (S)-(6,6'-dimethyl-2,2'-biphenylylene)bis(di-o-tolylphosphine), (R)- or (S)-(6,6'-dimethyl-2,2'-biphenylylene)bis(di-m-fluorophenylphosphine), (R)- or (S)-1,11-bis(diphenylphosphino)-5,7-dihydrodibenz[c,e]oxepin.

(R)-(6,6'-Dimethyl-2,2'-biphenylylene)bis(diphenylphosphine) is a particularly preferred compound of formula IV.

(R)-(1,1'-Binaphthyl)-2,2'-diylbis(diphenylphosphine) is a particularly preferred compound of formula V.

Among the preferred achiral triarylphosphines which come into consideration are those in which the three aryl residues are identical, preferably triphenylphosphine.

The isomerization in accordance with the invention can be carried out in any conventional organic solvents which are inert under the reaction conditions. As such there can be named, in particular, lower alkanols such as e.g. methanol or ethanol, aromatic hydrocarbons such as benzene or toluene, cyclic ethers such as tetrahydrofuran or dioxan, esters such as e.g. ethyl acetate or also mixtures thereof and the like.

As mentioned earlier, the isomerization in accordance with the invention is effected by means of a complex of formula III in the presence of an achiral triarylphosphine. Thus, the isomerization can be carried out by reacting the substrate to be isomerized together with the complex of formula III and the achiral triarylphosphine. Alternatively, the complex of formula III can also be first reacted with an achiral triarylphosphine and the product obtained, optionally after its isolation, can then be reacted with the substrate of formula II.

The isomerization can be carried out conveniently in an inert organic solvent and at a temperature of about room temperature to about 130° C. This reaction is preferably effected at an elevated temperature, i.e. depending on the solvent used either at the reflux temperature of the reaction mixture or in a closed vessel under pressure.

The molar ratio of complex of formula III to achiral triarylphosphine conveniently amounts to a ratio of from about 1:2 to about 1:10 preferrably from about 1:2 to about 1:4.

By means of the process in accordance with the invention, i.e. by the isomerization of the compounds of formula II with a complex of formula III in the presence of a triarylphosphine, the recyclization of the catalyst is substantially simplified and cheapened. At the same time, by the addition of the cheap and readily accessible triarylphosphine the life-span and the activity of the catalyst are considerably increased.

EXAMPLE 1

1 g (4.78 mmol) of N,N-diethylnerylamine, 20.3 mg (0.024 mmol) of [$\eta^4$-1,5-cyclooctadiene][(R)-6,6'-dimethyl-2,2'-biphenylylene)bis(diphenylphosphine)]-rhodium(I) tetrafluoroborate, 18.8 mg (0.072 mmol) of triphenylphosphine and 5 ml of absolute tetrahydrofuran are introduced into a 25 ml Schlenk tube. The Schlenk tube is tightly closed, de-gassed by three-fold freezing/evacuating, placed under nitrogen and heated at 100° C. in an oil-bath for 16 hours. Thereafter, the tetrahydrofuran is removed in a high vacuum (0.2 mbar), the catalyst is separated with 5 ml of pentane and the supernatant slightly red colored solution is pipetted into a flask. The residual red-brown powder is washed twice with 5 ml of pentane each time. The combined pentane solutions are concentrated and distilled in a bulb-tube oven (about 100° C./0.5 mbar). 0.95 g of a colorless oil are obtained. The distillate is treated at 0° C. with a three- -fold volume of 30% aqueous acetic acid, stirred vigorously for 15 minutes, covered with about 5 ml of pentane and stirred at room temperature for a further 15 minutes. After phase separation the aqueous phase is extracted a further twice with pentane. The combined organic phases are washed in succession with saturated $NaHCO_3$ solution, water and saturated NaCl solution, dried over $Na_2SO_4$, filtered and evaporated. After bulb-tube distillation at 100°–110° C./15 mbar there is obtained 0.6 g of (R)-citronellal (97% e.e. according to the gas-chromatographical method).

About 2 mg of the above rhodium complex and 2 mg of triphenylphosphine are added to the catalyst residue and reacted as previously described with the same amount of N,N-diethylnerylamine. There is obtained (R)-citronellal in practically the same yield with an e.e. content of 96.5%. Repeated recyclizations yield 0.58 g and 0.52 g of (R)-citronellal with e.e. contents of 96.2% and 96.8%, respectively.

EXAMPLE 2

N,N-Diethylnerylamine is isomerized in a manner analogous to Example 1, but using [$\eta^4$-1,5-cyclooctadiene][(R)-(1,1'-binaphthyl)-2,2'-diylbis(diphenylphosphine)]rhodium(I) tetrafluoroborate. There is obtained 0.61 g of (R)-citronellal with 97.2% e.e. according to the gas-chromatographical method.

The recyclizations of the catalyst, likewise carried out in a manner analogous to Example 1, lead to 0.59 g, 0.63 g and 0.57 g of (R)-citronellal with 97.5% e.e., 98.7% e.e. and 98.1% e.e., respectively.

What is claimed is:

1. A process of producing chiral enamines of the formula $$\text{R}\underset{*}{\diagup}\overset{CH_3}{\diagdown}\diagup\diagdown N\diagup\diagdown\overset{R^1}{\underset{R^2}{}} \quad \text{I}$$

wherein R is (a) $CH_3\diagdown C(CH_3)=CH-CH_2-[CH_2-CH(CH_3)-CH_2-CH_2-]_n$ (b) $CH_3-C(CH_3)(OH)-$ n is the number 0, 1 or 2; and the dotted bond can be optionally hydrogenated; and $R^1$ and $R^2$ are lower alkyl or cycloalkyl or when taken together with their attached nitrogen atom form a 5- or 6-membered heterocyclic ring; comprising isomerizing the E- or Z-form of a compound of the formula $$\text{R}\diagup\overset{CH_3}{\diagdown}=\diagdown\diagup N\diagup\diagdown\overset{R^1}{\underset{R^2}{}} \quad \text{II}$$

wherein R, $R^1$ and $R^2$ are as above; with a rhodium-diphosphine complex of the general formula $$[Rh(L^1)(L^2)]^+ X^- \quad \text{III}$$

wherein $L^1$ is a chiral diphosphine ligand, $L^2$ is a bis-olefin and $X^-$ is a non-complexing anion; with the addition of an achiral triarylphosphine in an amount sufficient to provide a mole ratio of said rhodium-diphosphine complex to said achiral triarylphosphine of from about 1:2 to about 1:10.

2. The process of claim 1, wherein the chiral diphosphine ligand $L^1$ is an optically active compound of the formula which is present in either the (R)- or (S)-form

[Structure IV: biphenyl with $R^4$, $R^5$, $(R^6)_p$ substituents and two $P(-R^3)_2$ groups]

wherein $R^3$ is phenyl; $R^4$ and $R^5$, which can be the same or different, are hydrogen, lower alkyl, lower alkoxy, di-lower alkylamino or protected hydroxymethyl; or $R^5$ and $R^6$ taken together form the groups $-(-CH_2-)_m$, $-CH_2-O-CH_2-$, $\begin{array}{c}-CH_2\\ \diagdown\\ \diagup\\ -CH_2\end{array}N-R^7$ or $\begin{array}{c}-CH_2\\ \diagdown\\ \diagup\\ -CH_2\end{array}C\begin{array}{c}OR^8\\ \\ OR^8\end{array}$ m is a number of from 3 to 5; $R^7$ is lower alkyl, phenyl or benzyl; $R^8$ is lower alkyl or the two $R^8$'s taken together form lower alkylene, $R^6$ signifies methyl, lower alkoxy, di-lower alkylamino or fluorine; and p is the number 0, 1, 2 or 3.

3. The process of claim 2, wherein $R^3$ is unsubstituted phenyl or methyl- or fluoro-substituted phenyl; p is the number 0 or 1 and $R^6$ is methyl, fluorine or di-lower alkylamino.

4. The process of claim 3, wherein $R^4$ and $R^5$ are the same lower alkyl group.

5. The process of claim 3, wherein $R^4$ and $R^5$ taken together form $-CH_2-O-CH_2-$.

6. The process of claim 5, wherein (R)-(6,6'-dimethyl-2,2'-biphenylylene)bis-(diphenylphosphine) is the chiral diphosphine ligand $L^1$.

7. The process in claim 1, wherein $R^1$ and $R^2$ are ethyl and R is a residue of formula (a) in which n is 0.

8. The process of claim 1, wherein an achiral triarylphosphine in which the three aryl residues are identical is used as the achiral triarylphosphine.

9. The process of claim 8, wherein triphenylphosphine is the achiral triarylphosphine.

10. The process of claim 1, wherein the chiral diphosphine ligand $L^1$ is an optically active compound of the formula which is present in either its (R)- or (S)-form is:

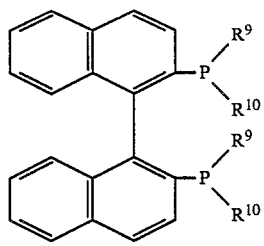

wherein $R^9$ and $R^{10}$ is phenyl or cyclohexyl and the naphthalene rings can be unsubstituted or substituted in the ortho-position with methyl, ethyl, halogen, di-lower alkylamino or lower alkoxy.

11. The process of claim 10, wherein (R)-(1,1'-binaphthyl)-2,2'-diylbis(diphenylphosphine) is used as the chiral diphosphine ligand $L^1$.

12. The process of claims 10, wherein $R^1$ and $R^2$ are ethyl and R is a residue of formula (a) in which n is 0.

13. The process of claims 10, wherein an achiral triarylphosphine in which the three aryl residues are identical is the achiral triarylphosphine.

14. The process of claim 10, wherein triphenylphosphine is used as the achiral triarylphosphine.

* * * * *